(12) United States Patent
Blackwood et al.

(10) Patent No.: US 9,378,925 B2
(45) Date of Patent: *Jun. 28, 2016

(54) TEM SAMPLE PREPARATION

(71) Applicant: FEI Company, Hillsboro, OR (US)

(72) Inventors: Jeffrey Blackwood, Portland, OR (US);
Matthew Bray, Portland, OR (US);
Corey Senowitz, San Diego, CA (US);
Cliff Bugge, Portland, OR (US)

(73) Assignee: FEI Company, Hillsboro, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/869,553

(22) Filed: Sep. 29, 2015

(65) Prior Publication Data

US 2016/0020069 A1    Jan. 21, 2016

Related U.S. Application Data

(63) Continuation of application No. 14/502,522, filed on Sep. 30, 2014, now Pat. No. 9,177,760, which is a continuation of application No. 13/981,563, filed as application No. PCT/US2012/023053 on Jan. 28, 2012, now Pat. No. 8,859,998.

(60) Provisional application No. 61/437,474, filed on Jan. 28, 2011.

(51) Int. Cl.
*H01J 37/00* (2006.01)
*H01J 37/305* (2006.01)
(Continued)

(52) U.S. Cl.
CPC ............ *H01J 37/3056* (2013.01); *G01N 1/286* (2013.01); *H01J 37/261* (2013.01); *G01N 2001/2886* (2013.01); *H01J 2237/31745* (2013.01)

(58) Field of Classification Search
CPC ....................... G01N 1/286; G01N 2001/3886
USPC .............................. 250/310, 311, 492.1–492.3
See application file for complete search history.

(56) References Cited

U.S. PATENT DOCUMENTS 7,388,218 B2   6/2008   Carleson
7,423,263 B2   9/2008   Hong et al.
(Continued)

FOREIGN PATENT DOCUMENTS

CN        1635365 A      7/2005
CN      101644639 A      2/2010
(Continued)

OTHER PUBLICATIONS

Giannuzzi, L. A., et al., "FIB Lift-Out Specimen Preparation Techniques," Introduction to Focused Ion Beams, 2005, 29 pages.
(Continued)

*Primary Examiner* — Michael Maskell
(74) *Attorney, Agent, or Firm* — John B. Kelly; Scheinberg & Associates

(57) ABSTRACT

An improved method of preparing ultra-thin TEM samples that combines backside thinning with an additional cleaning step to remove surface defects on the FIB-facing substrate surface. This additional step results in the creation of a cleaned, uniform "hardmask" that controls the ultimate results of the sample thinning, and allows for reliable and robust preparation of samples having thicknesses down to the 10 nm range.

15 Claims, 12 Drawing Sheets

(51) Int. Cl.
*G01N 1/28* (2006.01)
*H01J 37/26* (2006.01)

(56) References Cited

U.S. PATENT DOCUMENTS

| | | |
|---|---|---|
| 7,511,282 B2 | 3/2009 | Agorio et al. |
| 7,622,714 B2 | 11/2009 | Yaguchi et al. |
| 7,718,981 B2 | 5/2010 | Takahashi et al. |
| 8,087,379 B2 | 1/2012 | Chandler et al. |
| 8,134,124 B2 | 3/2012 | Blackwood et al. |
| 8,278,220 B2 | 10/2012 | Holtermann et al. |
| 8,525,137 B2 | 9/2013 | Blackwood et al. |
| 8,729,469 B1 | 5/2014 | Schmidt et al. |
| 8,859,998 B2 * | 10/2014 | Blackwood ............ G01N 1/286 250/492.1 |
| 2002/0088947 A1 | 7/2002 | Moran |
| 2006/0011867 A1 | 1/2006 | Kidron et al. |
| 2006/0011868 A1 | 1/2006 | Kidron et al. |
| 2008/0296498 A1 | 12/2008 | Hong |
| 2013/0143412 A1 | 6/2013 | Moriarty et al. |
| 2013/0248354 A1 | 9/2013 | Keady et al. |

FOREIGN PATENT DOCUMENTS

| | | |
|---|---|---|
| JP | 2007164992 A | 6/2007 |
| JP | 2007248082 A | 9/2007 |
| JP | 2008014899 A | 1/2008 |

OTHER PUBLICATIONS

Kang, Hyo-Jin, et al., "Ultra-Thin TEM Sample Preparation with Advanced Backside FIB Milling Method," Microsc. Microanal., 2010, pp. 170-171, vol. 16, No. 2.

* cited by examiner

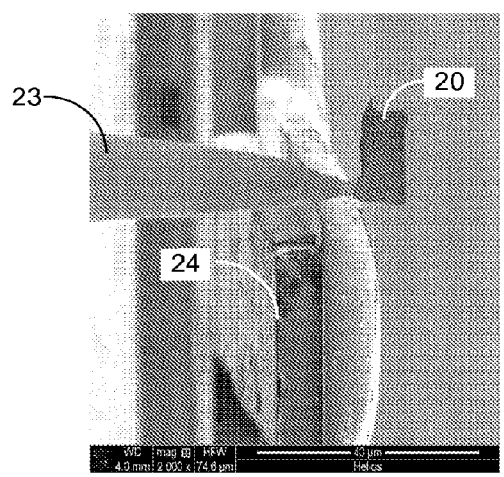
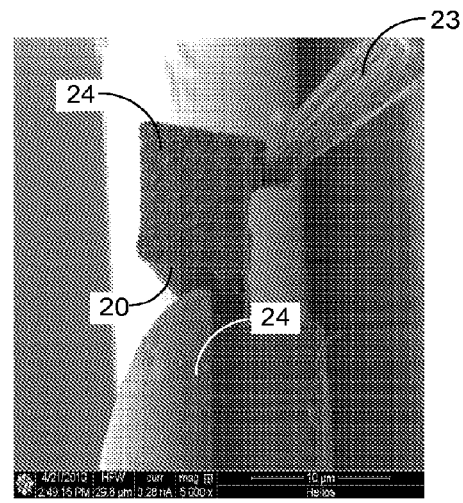
FIG. 4A          FIG. 4B
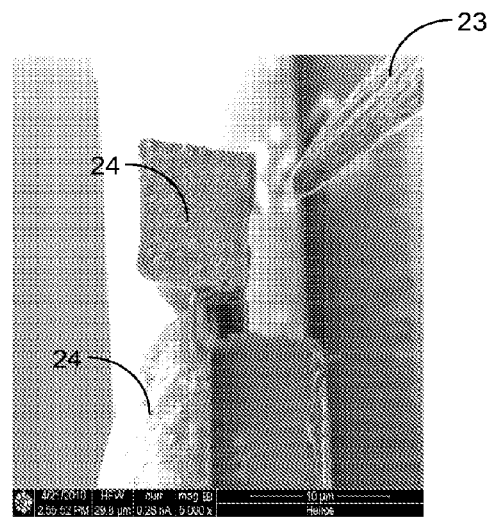
FIG. 4C

TEM SAMPLE PREPARATION

This application claims priority from U.S. patent application Ser. No. 14/502,522 filed Sep. 30, 2014, which is a continuation application of U.S. patent application Ser. No. 13/981,563 filed Aug. 16, 2013, which is a 371 national stage filing from international application PCT/US2012/023053, filed Jan. 28, 2012, which claims priority from U.S. Provisional Application 61/437,474, filed Jan. 28, 2011, which is hereby incorporated by reference.

TECHNICAL FIELD OF THE INVENTION

The present invention relates to preparation of samples for transmission electron microscopes and, in particular, to preparation of samples having a thickness of 30 nm or less.

BACKGROUND OF THE INVENTION

As semiconductor geometries continue to shrink, manufactures increasingly rely on Transmission electron microscopes (TEMs) for monitoring the process, analyzing defects, and investigating interface layer morphology. Transmission electron microscopes (TEMs) allow observers to see features having sizes on the order of nanometers. In contrast to SEMs, which only image the surface of a material, TEM also allows analysis of the internal structure of a sample. In a TEM, a broad beam impacts the sample and electrons that are transmitted through the sample are focused to form an image of the sample. The sample must be sufficiently thin to allow many of the electrons in the primary beam to travel though the sample and exit on the opposite site.

Because a sample must be very thin for viewing with transmission electron microscopy (whether TEM or STEM), preparation of the sample can be delicate, time-consuming work. The term "TEM" as used herein refers to a TEM or a STEM and references to preparing a sample for a TEM are to be understood to also include preparing a sample for viewing on an STEM. The term "STEM" as used herein also refers to both TEM and STEM.

TEM samples are typically less than 100 nm thick, but for some applications samples must be considerably thinner. With advanced processes at 30 nm and below, the sample needs to be less than 20 nm in thickness in order to avoid overlap among small scale structures. Currently thinning below 30 nm is difficult and not robust. Thickness variations in the sample result in sample bending, overmilling, or other catastrophic defects. For such small samples, preparation is a critical step in TEM analysis that significantly determines the quality of structural characterization and analysis of the smallest and most critical structures.

Even though the information that can be discovered by TEM analysis can be very valuable, the entire process of creating and measuring TEM samples has historically been so labor intensive and time consuming that it has not been practical to use this type of analysis for manufacturing process control. While the use of FIB methods in sample preparation has reduced the time required to prepare samples for TEM analysis down to only a few hours, it is not unusual to analyze 15 to 50 TEM samples from a given wafer. As a result, speed of sample preparation is a very important factor in the use of TEM analysis, especially for semiconductor process control.

A significant problem for the preparation of ultra thin (<30 nm thick) TEM samples is commonly referred to as "curtaining," in which non-uniform high-density materials on the surface of an integrated circuit produce a non-planar face on the TEM sample after thinning. Top-down thinning of a sample having these types of structural or density variations will cause vertical ridges to propagate from the denser materials (i.e. metal lines) near the top of the sample (the top being defined as closest to the ion beam source) down the face of the cross-section, running in a direction parallel to the ion beam direction. Curtaining is most often observed in semiconductor materials where multiple patterned layers of materials having a low sputtering yield blocks a faster sputtering yield material. Curtaining may also be observed in materials exhibiting different topographic regions where changes in sputtering yields vary with the milling incident angle. Curtaining artifacts reduce the quality of the TEM imaging and limit the minimal useful specimen thickness. For ultra-thin TEM samples, defined herein as samples having a thickness of less than 30 nm, the two cross-section faces are obviously in very close proximity so thickness variations from curtaining effects can cause a sample to be unusable. FIGS. 1A and 1B show photomicrographs of thinned samples showing curtaining on the sample faces.

In order to minimize curtaining in TEM sample preparation, it is known to invert the samples so that the bottom of the sample (the substrate) is facing the FIB column. Because the substrate portion of the sample will not have imbedded features such as metal lines or transistors, curtaining artifacts will not be introduced into the portion of the sample face containing the region of interest, i.e., the layers of circuitry on the top surface of the semiconductor. While this technique works reasonably well for TEM samples having a thickness of 50 to 100 nm, for ultra-thin samples having a sample thickness of 30 nm or less, even samples prepared by inverting the sample before thinning often show milling artifacts resulting in a undesirably non-uniform sample face.

Thus, there is still a need for an improved method of TEM sample preparation to allow the preparation of ultra-thin TEM samples.

SUMMARY OF THE INVENTION

It is an object of the invention, therefore, to provide an improved method of preparing ultra-thin TEM samples. Preferred embodiments of the present invention combine the current backside thinning process with an additional cleaning step to remove surface defects on the FIB-facing substrate surface. This additional step results in the creation of a cleaned, uniform "hardmask" that controls the ultimate results of the sample thinning, and allows for reliable and robust preparation of samples having thicknesses down to the 10 nm range.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIGS. 4A-4C are photomicrograph images showing the sequence of mounting an inverted TEM sample on a TEM sample grid;

The accompanying drawings are not intended to be drawn to scale. In the drawings, each identical or nearly identical component that is illustrated in various figures is represented by a like numeral. For purposes of clarity, not every component may be labeled in every drawing.

DETAILED DESCRIPTION OF PREFERRED EMBODIMENTS

Figure 1A:
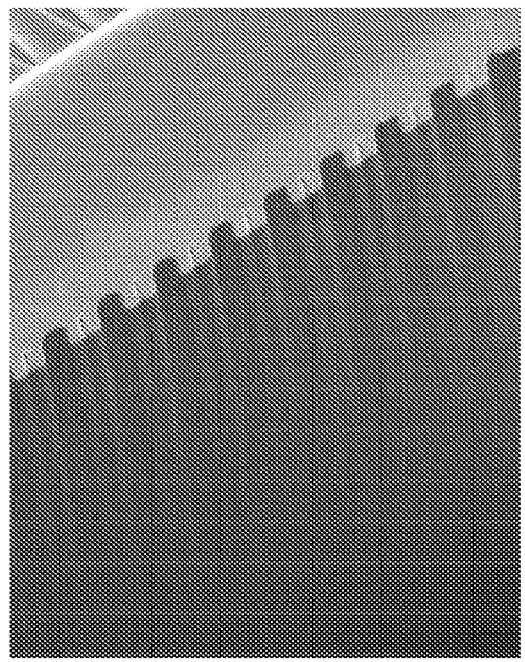
FIG. 1A is a photomicrograph of a thinned TEM sample showing curtaining.
Figure 1B:
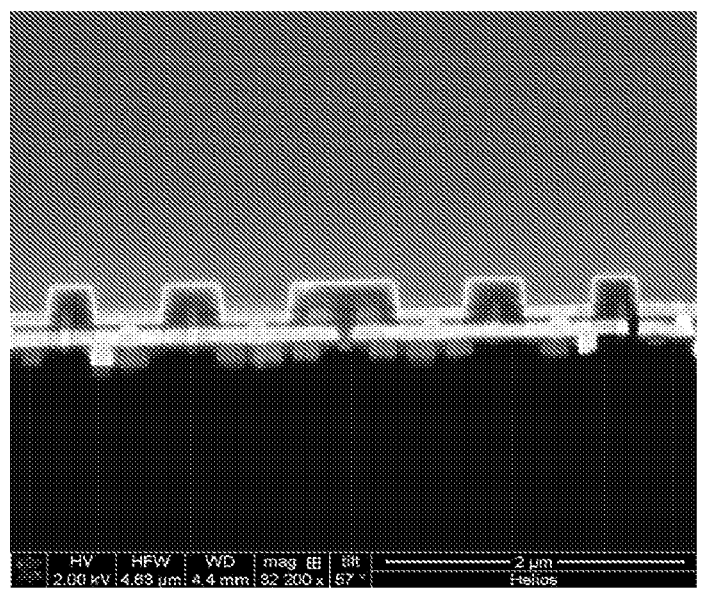
FIG. 1B is a photomicrograph of an inverted TEM sample where the curtaining is outside the region of interest.

Preferred embodiments of the present invention are directed at a novel method of preparing ultra-thin TEM samples. Preferred embodiments of the present invention combine the current backside thinning process with an additional cleaning step to remove surface defects on the FIB-facing substrate surface. During the typical TEM sample extraction process, the bottom surface of the sample will accumulate redeposited material from the sample extraction ion milling process. Non-uniformities on the bottom surface can also result from milling artifacts accrued during the bulk material removal process. Applicants have discovered that these material or topographical variations on the surface of the substrate side of the sample have a significant effect upon the TEM sample thinning process. These types of surface variations propagate through the milling process as the TEM sample (also referred to as a lamella) is thinned and result in sidewall non-uniformities that limit the minimum thickness to which the sample may be thinned. Applicants have discovered that these types of non-uniformities have resulted in the historically limited success of thinning samples thinner than 30 nm.

Preferred embodiments of the present invention introduce an additional step to the preparation of a backside thinned TEM sample in which the FIB-facing substrate surface is "cleaned" with the FIB to form a uniform backside substrate surface. As described in greater detail below, the FIB can be used to mill away the "dirty" substrate surface, forming a cleaned, uniformly flat substrate surface that functions as a sort of "hard mask" during TEM sample thinning in that it protects the region of interest below (when the sample is inverted) and it controls the creation of a smooth, flat TEM sample face. The additional step of forming the hard mask, while undesirably increasing the amount of time required to prepare a TEM sample, allows for reliable and robust preparation of samples having thicknesses down to the 10 nm range. The reliability of the methods described herein make the methods especially suitable for automated sample preparation.

While it is desirable that the flat surface formed by milling away a portion of the sample backside be as uniformly flat as possible to avoid introducing irregularities or artifacts during lamella thinning, skilled persons will recognize that this desire must be weighed against the increased time and expense of producing TEM samples. Applicants have discovered, as described in greater detail below, that using an ion beam, for example a 30 kV gallium ion beam, to mill away or "cut off" a portion of the bottom of the extracted sample typically produces a sufficiently smooth surface to prepare ultra-thin TEM samples. As used herein, the phrase "ultra-thin TEM samples" will be used to refer to samples where the entire lamella or a portion of the lamella (such as a "window" large enough for TEM imaging) is thinned to a thickness of 30 nm or less.

A preferred method or apparatus of the present invention has many novel aspects, and because the invention can be embodied in different methods or apparatuses for different purposes, not every aspect need be present in every embodiment. Moreover, many of the aspects of the described embodiments may be separately patentable.

Figure 9:
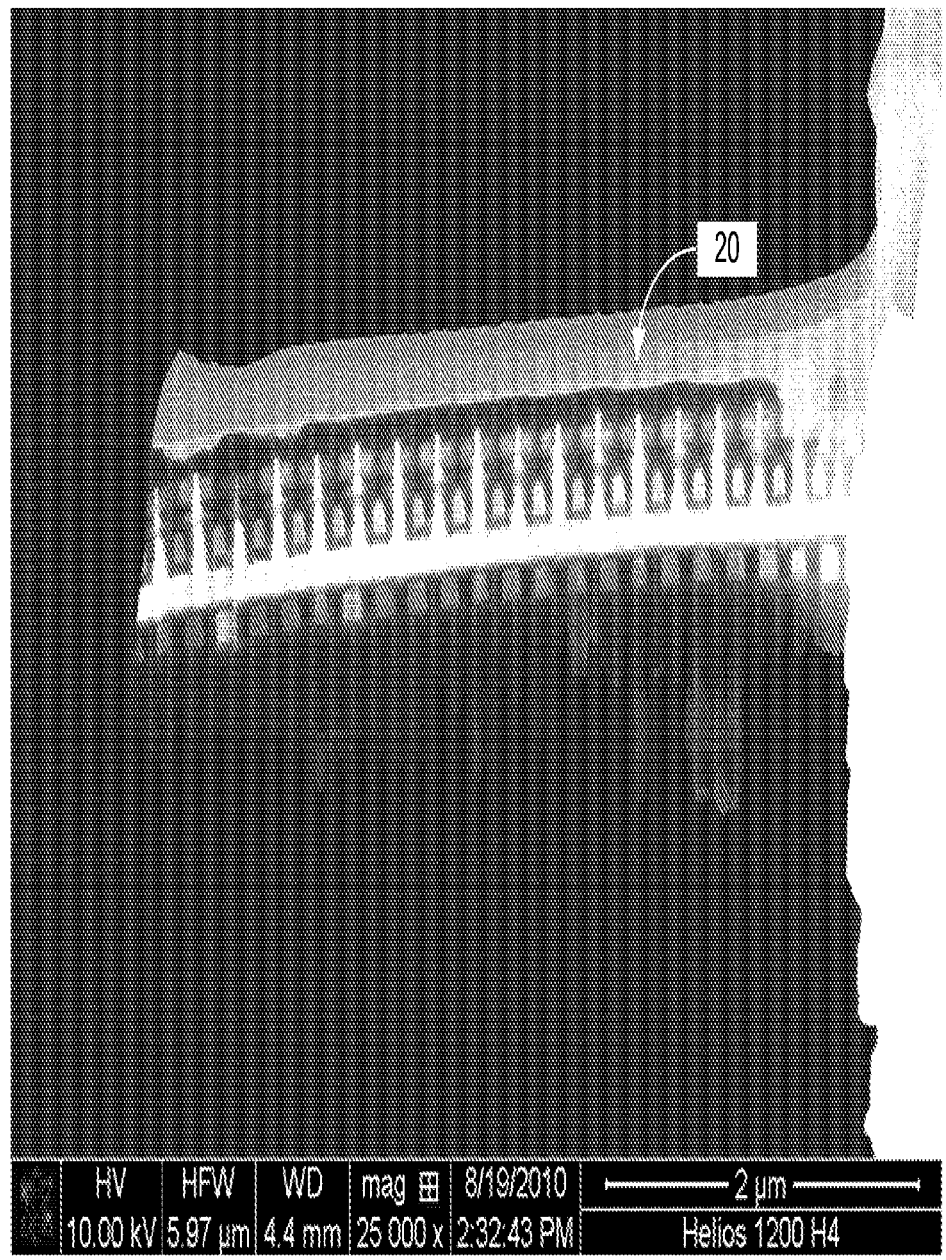
FIG. 9 shows a photomicrograph of a TEM sample ~20 nm thick produced without the substrate backside cleaning step.
Figure 10:
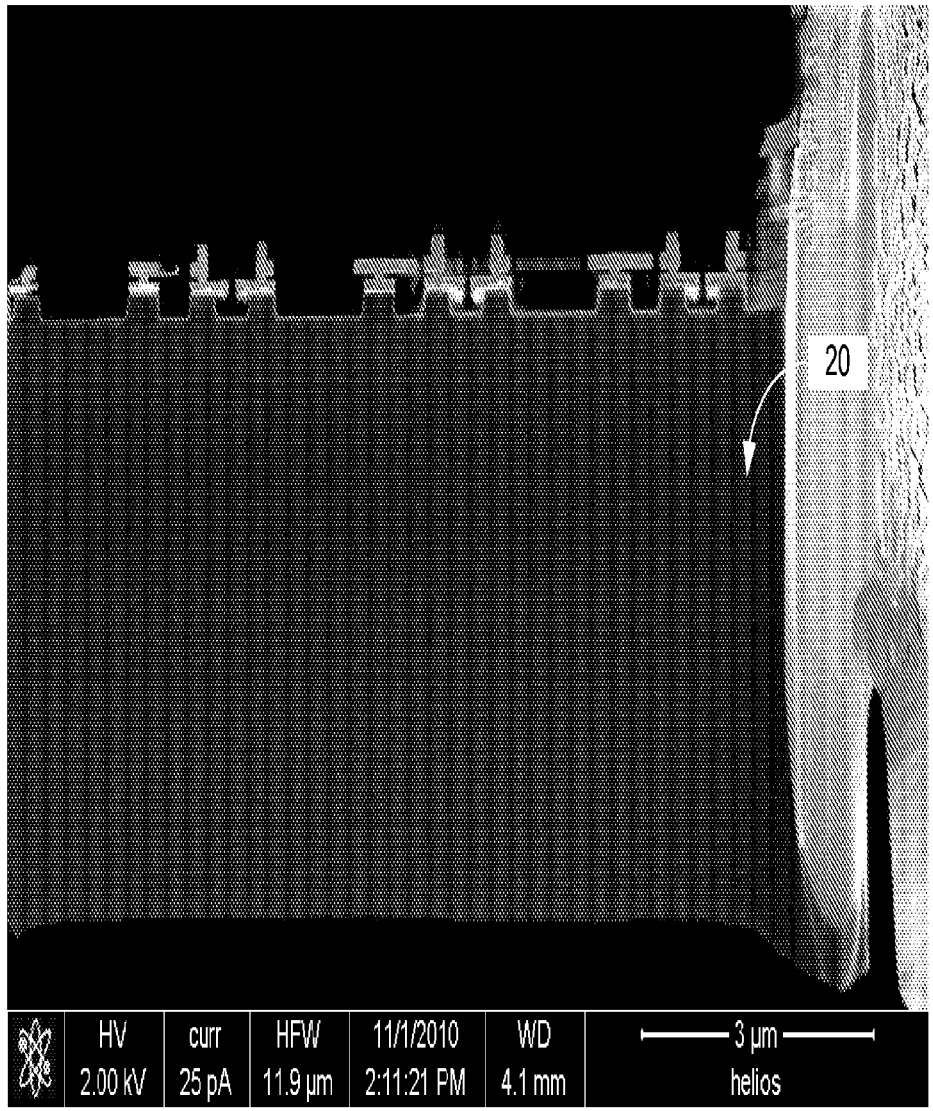
FIG. 10 shows a photomicrograph of a TEM sample <15 nm thick produced using the additional substrate backside cleaning step.
Figure 11:
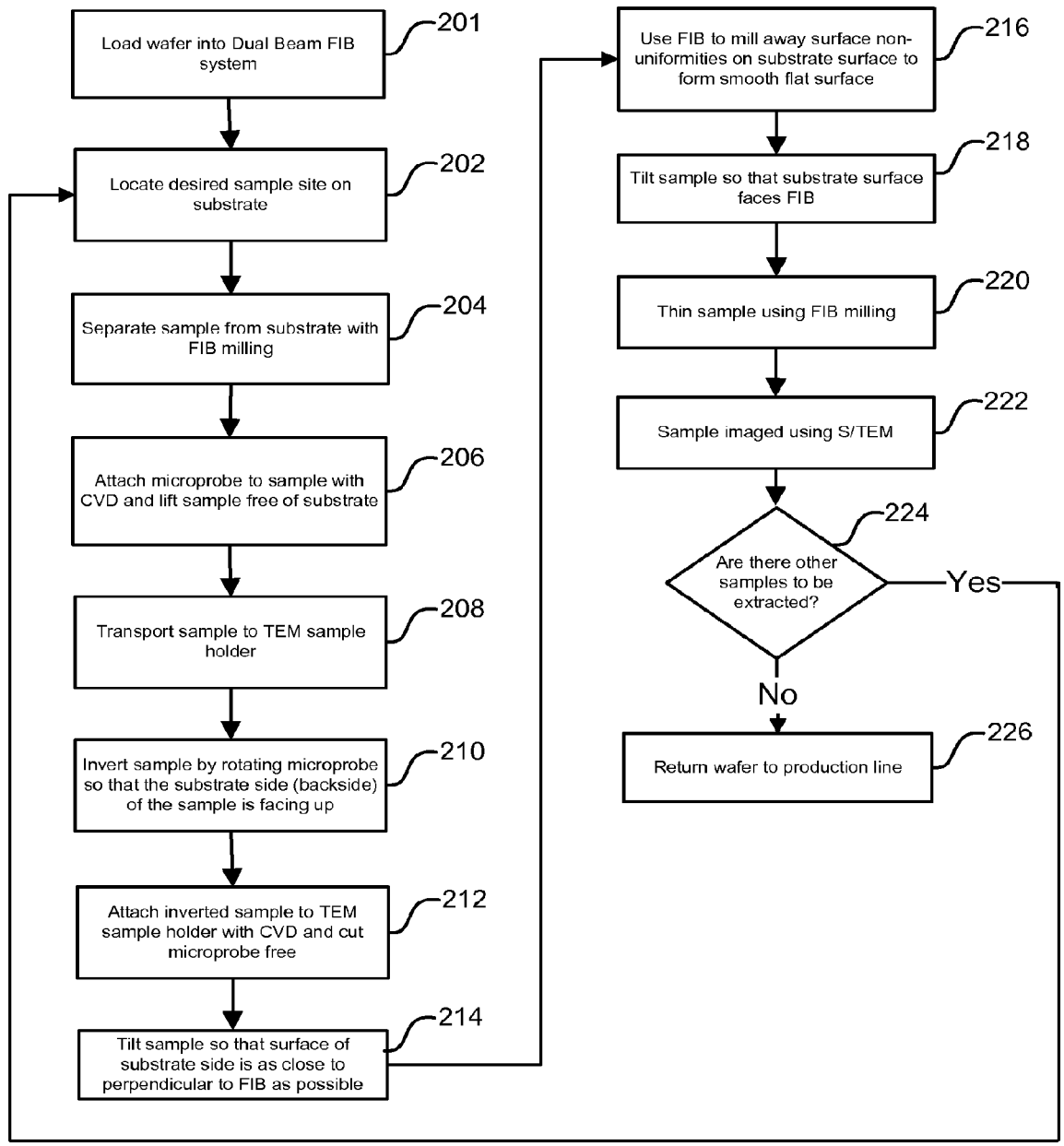
FIG. 11 is a flowchart showing the steps of creating an ultra thin TEM sample according to a preferred embodiment of the present invention.

FIG. 11 is a flowchart showing the steps of creating an ultra thin TEM sample according to a preferred embodiment of the present invention. Various steps in the process are shown in FIGS. 2 through 10.

Figure 12:
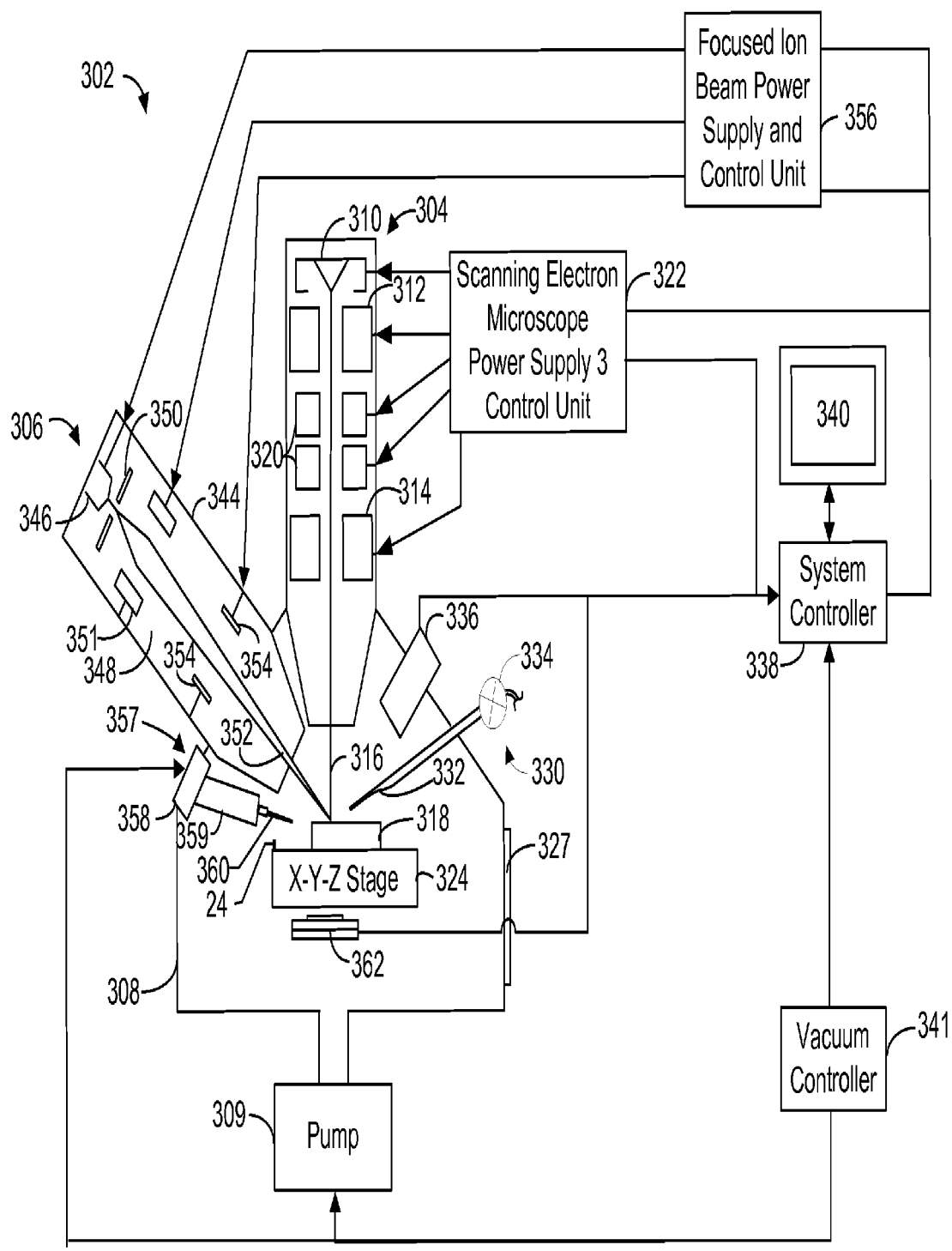
FIG. 12 shows a typical dual beam FIB/STEM system that could be used to implement the present invention.

First, in step 201, a substrate such as a semiconductor wafer is loaded into a Dual Beam FIB/STEM system having both a FIB column and a SEM column Referring also to FIG. 12, the typical dual-beam system 302 configuration is an electron column 304 having a vertical axis with an ion column 306 having an axis tilted with respect to the vertical (usually at a tilt of approximately 52 degrees). Wafers are preferably transferred by way of a multi-wafer carrier and auto-loading robot (not shown), as in well known in the art, although wafers can also be transferred manually.

In step 202, the location of a sample (containing a feature of interest) to be extracted from a substrate is determined. For example, the substrate may be a semiconductor wafer or portion thereof and the portion to be extracted may include a portion of an integrated circuit that is to be observed using the TEM. The location of the sample can be determined using a variety of methods known in the prior art. For example, the sample location can be located using coordinates based on CAD data for the semiconductor wafer. Lamella sites on the wafer surface can also be located automatically using image recognition software. Suitable image recognition software is available, for example, from Cognex Corporation of Natick, Mass. Image recognition software can be "trained" to locate the desired lamella locations by using sample images of similar features or by using geometric information from CAD data.

Figure 2:
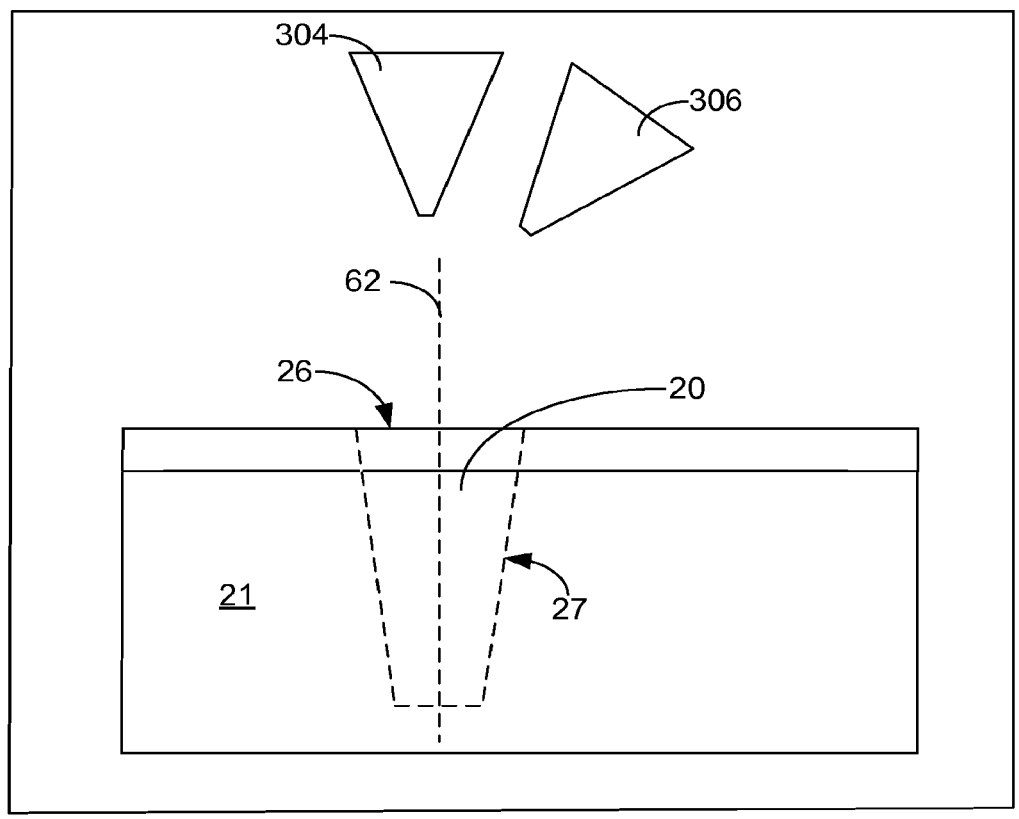
FIG. 2 is a schematic representation showing the location of a TEM sample to be extracted within a larger substrate.
Figure 3A:
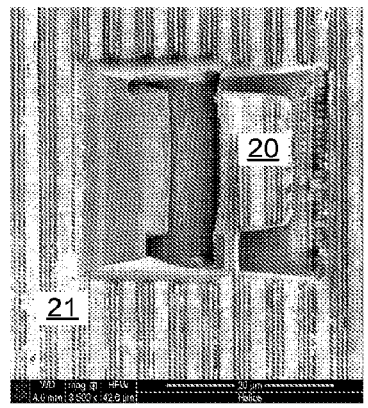
FIGS. 3A-3D are photomicrograph images showing the sequence of a typical in-situ lift out of a chunk-type TEM.
Figure 3B:
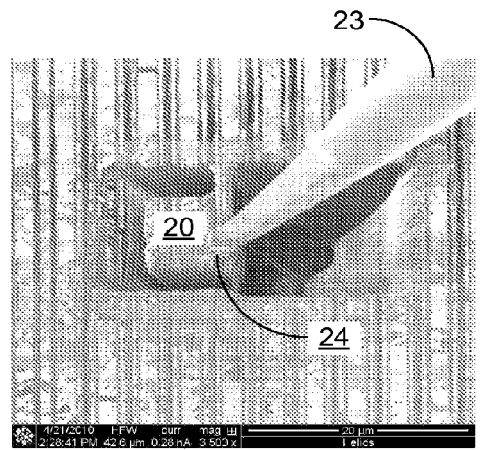
Figure 3C:
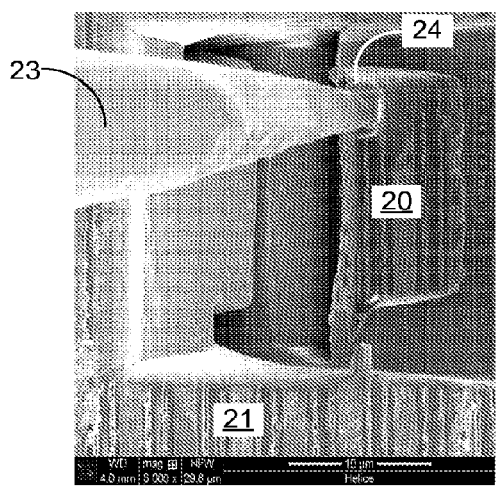
Figure 3D:
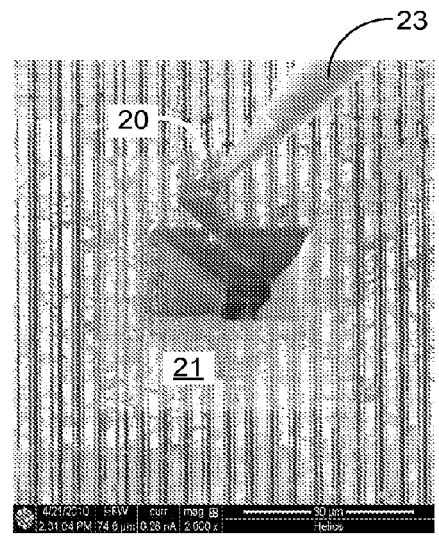

FIG. 2 is a schematic representation showing the location of the sample 20 to be extracted within a larger substrate 21. For convenience, the upper portion of the sample oriented toward the substrate surface closest to the charged particle beams will be referred to herein as the "top" of the sample 26, even after the sample is removed from the substrate and its orientation changed. Likewise, the lower portion of the sample oriented away from the substrate surface closest to the charged particle beams and toward the bulk substrate material will be referred to herein as the "bottom" of the sample 27, even after the sample is removed from the substrate and its orientation changed. The vertical axis of the sample is shown by dashed line 62.

In step 204, the sample 20 is completely or partially separated from the substrate 21 by milling with a focused ion beam. As discussed below, this step can be accomplished by using a dual beam FIB/SEM system such as the Helios1200 Expida™ 1255 DualBeam™ System, available from FEI Company of Hillsboro, Oreg., the assignee of the present invention. Next, a microprobe tip 23 is attached to the sample by FIB-induced chemical vapor deposition. In the case of only partially separated samples, the sample is then completely freed by further FIB milling. This process typically results in a wedge-shaped sample 20, which is approximately 10×5×5 μm in size. In step 206, the sample 20 is then lifted free of the substrate 21 by the attached microprobe 23. This sequence is shown sequentially in the photomicrographs of FIGS. 3A to 3D.

In step 208, the sample is then transported by the attached microprobe to a TEM sample holder 24 as shown in FIG. 4A. Sample holder 24 can comprise, for example, a TEM finger grid. Referring also to FIG. 12, the TEM sample holder is preferably mounted vertically onto a stage so that the vertical axis 64 of TEM sample holder 24 is perpendicular to the plane of the sample stage surface. In the embodiment shown in FIG. 4A, the vertical axis 62 of the sample is substantially parallel to the vertical axis 64 of the TEM sample holder 24. Although other orientations are possible, this orientation is described herein for simplicity.

Figure 5:
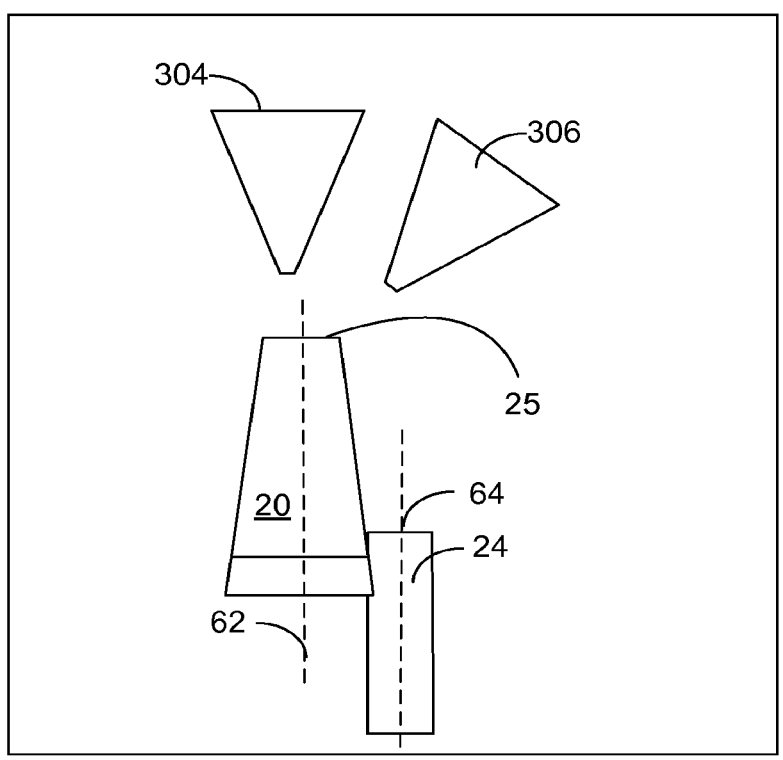
FIG. 5 is a schematic representation showing the inverted TEM sample mounted on a TEM sample grid.

In step 210, the sample is then inverted by rotating the microprobe so that the substrate side 25 of the sample is facing up (also referred to as the backside). In other words, the sample is rotated around an axis perpendicular to the sample's vertical axis in order to invert the top and bottom sides of the sample. FIG. 4B shows a top down view of the sample in close proximity to the TEM sample holder. In step 212, the sample 20 is attached to the sample holder 24 (again with FIB-induced CVD) and then end of the sample where the microprobe 23 is attached is cut free, as shown in FIG. 4C. FIG. 5 is a schematic representation showing the inverted TEM sample mounted on a TEM sample grid.

As shown in photomicrographs 4B and 4C, the substrate backside (facing up after the sample is inverted) has substantial non-uniformities resulting from redeposition or from milling artifacts. This "dirty" substrate face has been rotated up by inverting the sample and faces the FIB. Applicants have discovered that these non-uniformities on the substrate backside have a significant impact upon the ultimate result of thinning a sample to a thickness of 30 nm or less. Thus, in step 214 the sample is tilted so that the FIB will be as perpendicular as possible to the substrate backside surface given the stage/manipulator used in the FIB system. This is shown schematically in FIG. 6. In the system shown in FIG. 6, the TEM sample holder 24 has been tilted from 0 degrees (vertical) to roughly 90 degrees (horizontal). In step 216, the FIB is then used to mill away the substrate backside surface at the angle indicated by cut line 28. The actual amount of material to be removed will depend upon the surface irregularities present.

Figure 6:
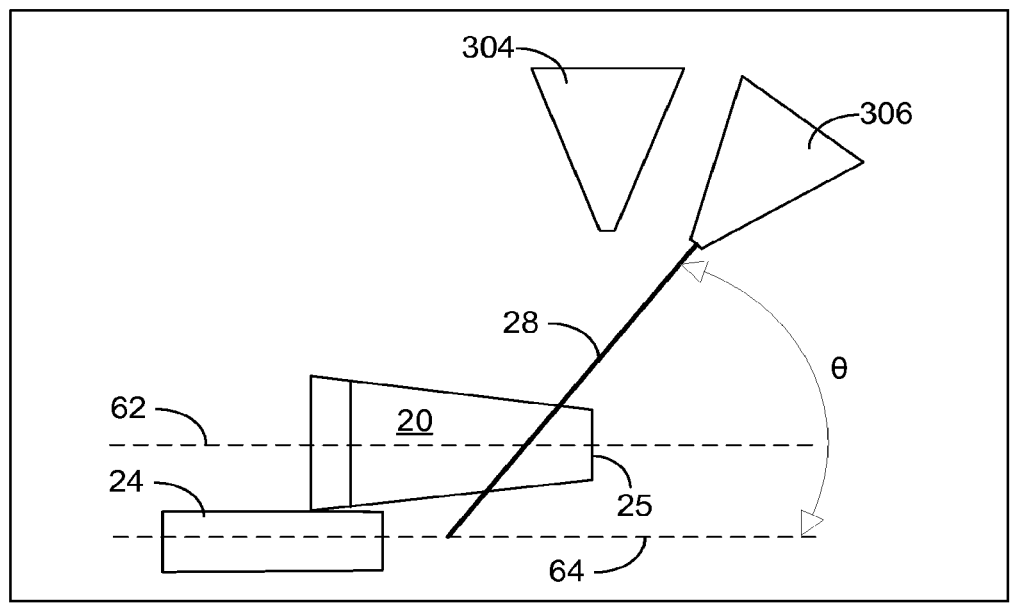
FIG. 6 is a schematic representation showing the inverted TEM sample tilted so that the FIB can be used to clean the substrate backside surface.

If the FIB is at 52 degrees with respect to the vertical axis of the SEM column, that would make the cut line 28 of the FIB at an angle of approximately 38 degrees relative to the axis 64 of the sample holder 24 (and thus to the vertical axis 62 of the sample). While the FIB cut line 28 in FIG. 6 is not perpendicular to the substrate backside surface, a cleaning cut at this angle would still be sufficient to remove the sample surface non-uniformities described above and produce a uniformly flat backside surface. The use of the term "uniformly flat" is intended to convey that after milling the backside surface is planar and free from any significant irregularities. The term is not intended to imply that the flat surface is necessarily perpendicular to the sample vertical axis. In fact, as described herein, the angle of the flat backside surface in relation to the vertical axis of the sample can be anywhere within a wide range of angles, preferably anywhere from 35 to 90 degrees.

The substrate backside surface can be smoothed or flattened by using the FIB at a lower operating accelerating voltage to mill away or cut off the bottom portion of the extracted sample. This serves to remove the non-uniformities on the surface without causing significant redeposition or milling artifacts, resulting in a post-cut clean and smooth substrate backside surface. Preferably, the backside milling is accomplished using, for example with a 5 kV FIB, rather than the ~30 kV FIB typically used for bulk material removal. However, Applicants have discovered that this step is not especially sensitive to FIB beam damage and so low-kV FIB milling is not always required for cleaning the backside surface. In other words, removing a portion of the backside surface using a 30 kV FIB will often produce a sufficiently smooth surface to greatly improve the quality of the lamella. The desire for a smoother surface will have to be weighed against the increased production time to determine which approach is optimal in a given circumstance.

Figure 7A:
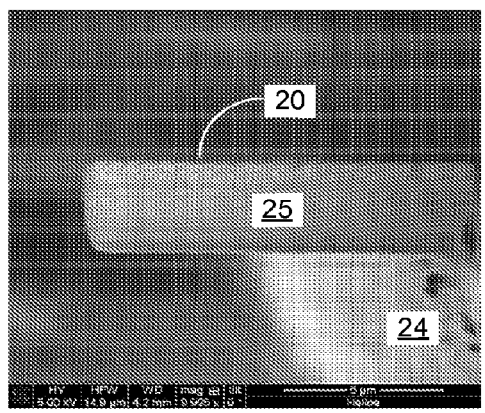
FIG. 7A shows a top down photomicrograph of a substrate backside surface before cleaning.
Figure 7B:
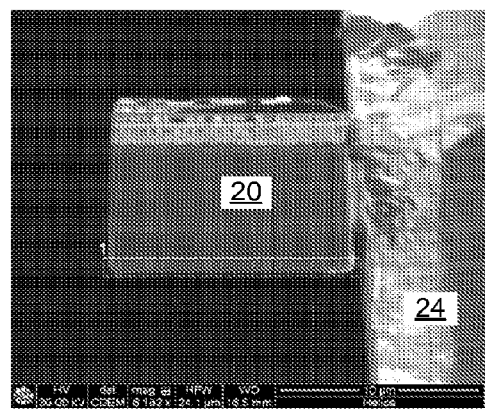
FIG. 7B is a photomicrograph of a side view of the sample of FIG. 7A showing the location of the FIB cut line.
Figure 7C:
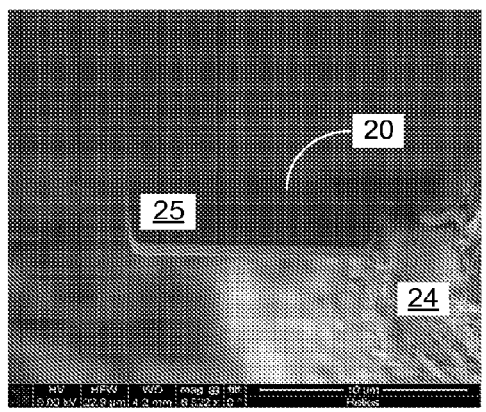
FIG. 7C is a top down photomicrograph of the substrate backside surface of FIG. 7A after the FIB cleaning cut and with substantially all of the non-uniformities on the substrate backside surface removed.

FIG. 7A shows a top down photomicrograph of a substrate backside surface 25 before the cleaning cut described above. FIG. 7B is a photomicrograph of a side view of the sample 20 of FIG. 7A, with the location of the cut line shown by dashed line 28. And finally, FIG. 7C is a top down photomicrograph of the substrate backside surface 25 of FIG. 7A after the FIB cleaning cut (using a 5 kV FIB) and with substantially all of the non-uniformities on surface 25 removed.

Figure 8A:
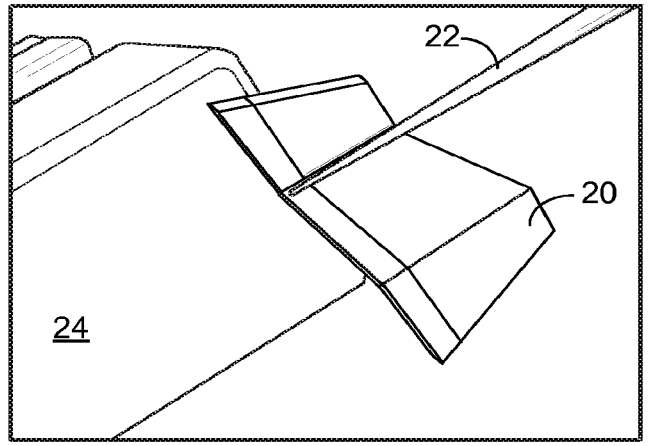
FIGS. 8A and 8B show the process of thinning a sample after the FIB has been used to clean the substrate backside surface.
Figure 8B:
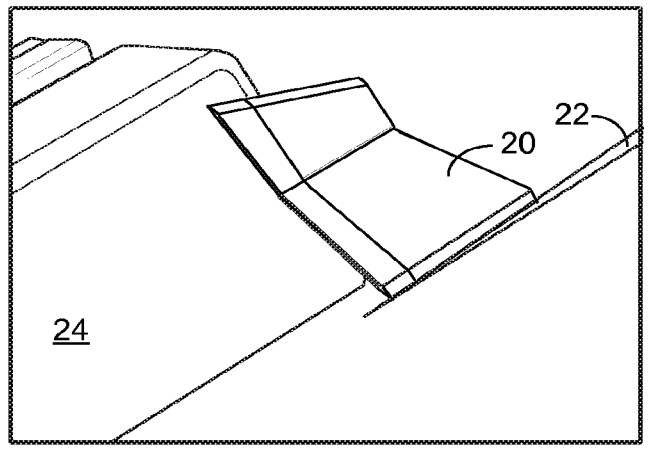

In step 218, once a more uniform substrate backside surface has been formed, the sample can be tilted back so that substrate backside surface again faces the FIB beam. Then in step 220, the sample is thinned, preferably from both sides, into an electron-transparent thin section by milling with the ion beam as shown in FIGS. 8A-8B. The uniform FIB-facing surface produced as described above eliminates cross-section thickness variations on both sides of the TEM sample. FIG. 9 shows a photomicrograph of a TEM sample ~20 nm thick produced without the substrate backside cleaning step. As shown in FIG. 9, there are substantial thickness variations in this TEM sample. FIG. 10, however, shows a cross-section photomicrograph of a TEM sample <15 nm thick produced using the additional substrate backside-cleaning step. The thickness variations seen in the sample of FIG. 9 are not present in FIG. 10, as shown by the lack of curtaining on the sample in FIG. 10, even though the sample in FIG. 10 is at least 25% thinner than the sample of FIG. 9.

Finally, in step 222, the sample 20 can be imaged using the electron beam and TEM detector, either in the dual beam system or after transport to a separate TEM instrument.

FIG. 12 depicts one embodiment of an exemplary dual beam SEM/FIB system 302 that is equipped to carry out a method according to the present invention. As discussed above, embodiments of the present invention can be used in a wide variety of applications where a material is deposited onto a target surface of a substrate, including the preparation of TEM samples from vitrified biological samples. Preparation and analysis of such a sample is typically performed in a dual beam electron beam/focused ion beam system such as the one now described. FIG. 17 depicts an exemplary dual beam system 302 that can be used to carry out embodiments of the invention. Suitable dual beam systems are commercially available, for example, from FEI Company, Hillsboro, Oreg., the assignee of the present application. While an example of suitable hardware is provided below, the invention is not limited to being implemented in any particular type of hardware.

Dual beam system 302 has a vertically mounted electron beam column 304 and a focused ion beam (FIB) column 306 mounted at an angle of approximately 52 degrees from the vertical on an evacuable specimen chamber 308. The specimen chamber may be evacuated by pump system 309, which typically includes one or more, or a combination of, a turbomolecular pump, oil diffusion pumps, ion getter pumps, scroll pumps, or other known pumping means.

The electron beam column 304 includes an electron source 310, such as a Schottky emitter or a cold field emitter, for producing electrons, and electron-optical lenses 312 and 314 forming a finely focused beam of electrons 316. Electron source 310 is typically maintained at an electrical potential of between 500 V and 30 kV above the electrical potential of a work piece 318, which is typically maintained at ground potential.

Thus, electrons impact the work piece 318 at landing energies of approximately 500 eV to 30 keV. A negative electrical potential can be applied to the work piece to reduce the landing energy of the electrons, which reduces the interaction volume of the electrons with the work piece surface, thereby reducing the size of the nucleation site. Work piece 318 may comprise, for example, a semiconductor device, microelectromechanical system (MEMS), or a lithography mask. The impact point of the beam of electrons 316 can be positioned on and scanned over the surface of a work piece 318 by means of deflection coils 320. Operation of lenses 312 and 314 and deflection coils 320 is controlled by scanning electron microscope power supply and control unit 322. Lenses and deflection unit may use electric fields, magnetic fields, or a combination thereof.

Work piece 318 is on movable stage 324 within specimen chamber 308. Stage 324 can preferably move in a horizontal plane (X and Y axes) and vertically (Z axis) and can tilt approximately sixty (60) degrees and rotate about the Z axis. A door 327 can be opened for inserting work piece 318 onto X-Y-Z stage 324 and also for servicing an internal gas supply reservoir (not shown), if one is used. The door is interlocked so that it cannot be opened if specimen chamber 308 is evacuated.

Mounted on the vacuum chamber are multiple gas injection systems (GIS) 330 (two shown). Each GIS comprises a reservoir (not shown) for holding the precursor or activation materials and a needle 332 for directing the gas to the surface of the work piece. Each GIS further comprises means 334 for regulating the supply of precursor material to the work piece. In this example the regulating means are depicted as an adjustable valve, but the regulating means could also comprise, for example, a regulated heater for heating the precursor material to control its vapor pressure.

When the electrons in the electron beam 316 strike work piece 318, secondary electrons, backscattered electrons, and Auger electrons are emitted and can be detected to form an image or to determine information about the work piece. Secondary electrons, for example, are detected by secondary electron detector 336, such as an Everhart-Thornley detector, or a semiconductor detector device capable of detecting low energy electrons. STEM detector 362, located beneath the TEM sample holder 24 and the stage 324, can collect electrons that are transmitted through a sample mounted on the TEM sample holder 24. Signals from the detectors 336, 362 are provided to a system controller 338. Said controller 338 also controls the deflector signals, lenses, electron source, GIS, stage and pump, and other items of the instrument. Monitor 340 is used to display user controls and an image of the work piece using the signal.

The chamber 308 is evacuated by pump system 309 under the control of vacuum controller 341. The vacuum system provides within chamber 308 a vacuum of approximately $3 \times 10^{-6}$ mbar. When a suitable precursor or activator gas is introduced onto the sample surface, the chamber background pressure may rise, typically to about $5 \times 10^{-5}$ mbar.

Focused ion beam column 306 comprises an upper neck portion 344 within which are located an ion source 346 and a focusing column 348 including extractor electrode 350 and an electrostatic optical system including an objective lens 351. Ion source 346 may comprise a liquid metal gallium ion source, a plasma ion source, a liquid metal alloy source, or any other type of ion source. The axis of focusing column 348 is tilted 52 degrees from the axis of the electron column. An ion beam 352 passes from ion source 346 through focusing column 348 and between electrostatic deflectors 354 toward work piece 318.

FIB power supply and control unit 356 provides an electrical potential at ion source 346. Ion source 346 is typically maintained at an electrical potential of between 1 kV and 60 kV above the electrical potential of the work piece, which is typically maintained at ground potential. Thus, ions impact the work piece at landing energies of approximately 1 keV to 60 keV. FIB power supply and control unit 356 is coupled to deflection plates 354 which can cause the ion beam to trace out a corresponding pattern on the upper surface of work piece In some systems, the deflection plates are placed before the final lens, as is well known in the art. Beam blanking electrodes (not shown) within ion beam focusing column 348 cause ion beam 352 to impact onto blanking aperture (not shown) instead of work piece 318 when a FIB power supply and control unit 356 applies a blanking voltage to the blanking electrode.

The ion source 346 typically provides a beam of singly charged positive gallium ions that can be focused into a sub one-tenth micrometer wide beam at work piece 318 for modifying the work piece 318 by ion milling, enhanced etch, material deposition, or for imaging the work piece 318.

A micromanipulator 357, such as the AutoProbe 200™ from Omniprobe, Inc., Dallas, Tex., or the Model MM3A from Kleindiek Nanotechnik, Reutlingen, Germany, can precisely move objects within the vacuum chamber. Micromanipulator 357 may comprise precision electric motors 358 positioned outside the vacuum chamber to provide X, Y, Z, and theta control of a portion 359 positioned within the vacuum chamber. The micromanipulator 357 can be fitted with different end effectors for manipulating small objects. In the embodiments described herein, the end effector is a thin probe 360. As is known in the prior art, a micromanipulator (or microprobe) can be used to transfer a TEM sample (which has been freed from a substrate, typically by an ion beam) to a TEM sample holder 24 for analysis.

System controller 338 controls the operations of the various parts of dual beam system 302. Through system controller 338, a user can cause ion beam 352 or electron beam 316 to be scanned in a desired manner through commands entered into a conventional user interface (not shown). Alternatively, system controller 338 may control dual beam system 302 in accordance with programmed instructions. FIG. 3 is a schematic representation, which does not include all the elements of a typical dual beam system and which does not reflect the actual appearance and size of, or the relationship between, all the elements.

According to preferred embodiments of the invention, a method of preparing a sample for TEM analysis, comprises:
loading a substrate into an ion beam system;
separating a sample from the substrate by ion beam milling;
extracting the sample from the substrate, said sample having a vertical axis, a top side, and a bottom side;
attaching the sample to a sample holder;
positioning the sample holder so that the ion beam is transverse to the vertical axis of the sample;
milling the bottom side of the sample to remove at least of portion of the bottom surface of the sample to produce a uniformly flat surface;
positioning the sample holder so that the bottom side of the sample is oriented toward the ion beam source and so that the ion beam is parallel to the vertical axis of the sample;
thinning the sample by directing the ion beam in a milling pattern that thins at least a portion of the sample to a thickness of 30 nm or less.

In some preferred embodiments, attaching the sample to a sample holder comprises: rotating the sample about an axis perpendicular to the sample vertical axis to invert the top and bottom sides of the sample; and attaching the inverted sample to a sample holder.

In some preferred embodiments, positioning the sample holder so that the ion beam is transverse to the vertical axis of the sample comprises positioning the sample holder so that the angle between the ion beam and the vertical axis of the sample is from 35 to 90 degrees.

In some preferred embodiments, thinning the sample by directing the ion beam in a milling pattern comprises thinning at least a portion of the sample to a thickness of 15 nm or less.

In some preferred embodiments, milling the bottom side of the sample to remove at least of portion of the bottom surface of the sample to produce a uniformly flat surface comprises removing at least the bottom 25 nm of the sample.

In some preferred embodiments, the substrate is a semiconductor wafer or portion thereof and the sample to be extracted is a portion of an integrated circuit that is to be observed using a TEM.

In some preferred embodiments, extracting the sample from the substrate comprises attaching a microprobe to the freed sample and extracting the sample from the substrate using the attached microprobe, and in which attaching the sample to a sample holder comprises attaching the sample to a sample holder and separating the microprobe from the attached sample. In some preferred embodiments, rotating the sample about an axis perpendicular to the sample vertical axis to invert the top and bottom sides of the sample comprises inverting the sample by rotating the microprobe so that the orientation of the top and bottom sides is reversed.

In some preferred embodiments, milling the bottom side of the sample to remove at least of portion of the bottom surface of the sample to produce a uniformly flat surface comprises milling the bottom side of the sample using an ion beam having a first accelerating voltage and then milling the bottom side of the sample at a second accelerating voltage, the second accelerating voltage being less than half of the first accelerating voltage. In some preferred embodiments, milling the bottom side of the sample to remove at least of portion of the bottom surface of the sample to produce a uniformly flat surface comprises milling the bottom side of the sample using an ion beam having an accelerating voltage of 5 kV or less. In some preferred embodiments, milling the bottom side of the sample to remove at least of portion of the bottom surface of the sample to produce a uniformly flat surface comprises milling the bottom side of the sample using an ion beam having an accelerating voltage of 30 kV or more.

Preferred embodiments of the present invention include an apparatus for carrying out the methods described herein. Preferred embodiments also include a non-transitory computer-readable storage medium configured with a computer program, where the storage medium so configured causes a computer to control a charged particle beam system to carry out the steps of the methods described herein.

According to preferred embodiments of the invention, a method of preparing an ultra thin TEM sample for TEM analysis, comprises:
loading a substrate into an ion beam system including an ion beam source and optics for focusing an ion beam along an axis and onto the substrate;
freeing a sample from the substrate by ion beam milling, said sample having a vertical axis, a top side closest to the ion beam source, and a bottom side opposite the ion beam source;
attaching a microprobe to the freed sample;
extracting the sample from the substrate using the attached microprobe;
inverting the sample by rotating the microprobe so that the orientation of the top and bottom sides is reversed;
attaching the inverted sample to a sample holder and separating the microprobe from the attached sample;
positioning the sample holder so that the ion beam axis is at an angle of 30 to 90 degrees relative to the vertical axis of the sample;
removing at least 25 nm from the bottom of the sample to produce a planar surface parallel to the ion beam axis;
positioning the sample holder so that the top side of the sample is oriented opposite the ion beam source and so that the ion beam axis is parallel to the vertical axis of the sample;
thinning the sample by directing the ion beam in a milling pattern that thins at least a portion of the sample to a thickness of 30 nm or less.

According to preferred embodiments of the invention, an apparatus for preparing ultra-thin TEM sample comprises:
an ion beam system including an ion beam source, optics for focusing an ion beam along an axis and onto a substrate, and a micromanipulator for manipulating a sample; and
a computer-readable memory storing computer instructions, the instructions including a program for controlling the apparatus and causing the apparatus to carry out the steps of:
locating a desired sample site on the substrate;
separating a sample from the substrate by ion beam milling;

extracting the sample from the substrate, said sample having a vertical axis, a top side, and a bottom side;
attaching the sample to a sample holder;
positioning the sample holder so that the ion beam is transverse to the vertical axis of the sample;
milling the bottom side of the sample to remove at least of portion of the bottom surface of the sample to produce a uniformly flat surface;
positioning the sample so that the bottom side of the sample is oriented toward the ion beam source and so that the ion beam is parallel to the vertical axis of the sample; and
thinning the sample by directing the ion beam in a milling pattern that thins at least a portion of the sample to a thickness of 30 nm or less.

Although the description of the present invention above is mainly directed at methods of preparing ultra thin TEM samples, it should be recognized that an apparatus performing the operation of such a method would further be within the scope of the present invention. Further, it should be recognized that embodiments of the present invention can be implemented via computer hardware, a combination of both hardware and software, or by computer instructions stored in a non-transitory computer-readable memory. The methods can be implemented in computer programs using standard programming techniques—including a non-transitory computer-readable storage medium configured with a computer program, where the storage medium so configured causes a computer to operate in a specific and predefined manner—according to the methods and figures described in this Specification. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits programmed for that purpose.

Further, methodologies may be implemented in any type of computing platform, including but not limited to, personal computers, mini-computers, main-frames, workstations, networked or distributed computing environments, computer platforms separate, integral to, or in communication with charged particle tools or other imaging devices, and the like. Aspects of the present invention may be implemented in machine readable code stored on a storage medium or device, whether removable or integral to the computing platform, such as a hard disc, optical read and/or write storage mediums, RAM, ROM, and the like, so that it is readable by a programmable computer, for configuring and operating the computer when the storage media or device is read by the computer to perform the procedures described herein. Moreover, machine-readable code, or portions thereof, may be transmitted over a wired or wireless network. The invention described herein includes these and other various types of computer-readable storage media when such media contain instructions or programs for implementing the steps described above in conjunction with a microprocessor or other data processor. The invention also includes the computer itself when programmed according to the methods and techniques described herein.

Computer programs can be applied to input data to perform the functions described herein and thereby transform the input data to generate output data. The output information is applied to one or more output devices such as a display monitor. In preferred embodiments of the present invention, the transformed data represents physical and tangible objects, including producing a particular visual depiction of the physical and tangible objects on a display.

Preferred embodiments of the present invention also make use of a particle beam apparatus, such as a FIB or SEM, in order to image a sample using a beam of particles. Such particles used to image a sample inherently interact with the sample resulting in some degree of physical transformation. Further, throughout the present specification, discussions utilizing terms such as "calculating," "determining," "measuring," "generating," "detecting," "forming," or the like, also refer to the action and processes of a computer system, or similar electronic device, that manipulates and transforms data represented as physical quantities within the computer system into other data similarly represented as physical quantities within the computer system or other information storage, transmission or display devices.

The invention has broad applicability and can provide many benefits as described and shown in the examples above. The embodiments will vary greatly depending upon the specific application, and not every embodiment will provide all of the benefits and meet all of the objectives that are achievable by the invention. Particle beam systems suitable for carrying out the present invention are commercially available, for example, from FEI Company, the assignee of the present application.

Although much of the previous description is directed at semiconductor wafers, the invention could be applied to any suitable substrate or surface. Further, whenever the terms "automatic," "automated," or similar terms are used herein, those terms will be understood to include manual initiation of the automatic or automated process or step. In the following discussion and in the claims, the terms "including" and "comprising" are used in an open-ended fashion, and thus should be interpreted to mean "including, but not limited to . . . ." The term "integrated circuit" refers to a set of electronic components and their interconnections (internal electrical circuit elements, collectively) that are patterned on the surface of a microchip. The term "semiconductor device" refers generically to an integrated circuit (IC), which may be integral to a semiconductor wafer, singulated from a wafer, or packaged for use on a circuit board. The term "FIB" or "focused ion beam" is used herein to refer to any collimated ion beam, including a beam focused by ion optics and shaped ion beams.

To the extent that any term is not specially defined in this specification, the intent is that the term is to be given its plain and ordinary meaning. The accompanying drawings are intended to aid in understanding the present invention and, unless otherwise indicated, are not drawn to scale.

Although the present invention and its advantages have been described in detail, it should be understood that various changes, substitutions and alterations can be made to the embodiments described herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method of preparing a sample for TEM analysis, the method comprising:
   positioning a sample having a vertical axis, a top side, and a bottom side so that an ion beam is transverse to the vertical axis of the sample;
   milling the bottom side of the sample to remove at least of portion of the bottom surface of the sample to produce a uniformly flat surface;
   positioning the sample so that the bottom side of the sample is oriented toward the ion beam source and so that the ion beam is parallel to the vertical axis of the sample;
   thinning the sample by directing the ion beam in a milling pattern that thins at least a portion of the sample to a thickness of 30 nm or less.

2. The method of claim 1 further comprising:
   rotating the sample about an axis perpendicular to the sample vertical axis to invert the top and bottom sides of the sample; and
   attaching the inverted sample to a sample holder.

3. The method of claim 1 in which positioning the sample so that the ion beam is transverse to the vertical axis of the sample comprises positioning the sample so that the angle between the ion beam and the vertical axis of the sample is from 35 to 90 degrees.

4. The method of claim 1 in which thinning the sample by directing the ion beam in a milling pattern comprises thinning at least a portion of the sample to a thickness of 15 nm or less.

5. The method of claim 1 in which milling the bottom side of the sample to remove at least of portion of the bottom surface of the sample to produce a uniformly flat surface comprises removing at least the bottom 25 nm of the sample.

6. The method of claim 1 in which the substrate is a semiconductor wafer or portion thereof and the sample to be extracted is a portion of an integrated circuit that is to be observed using a TEM.

7. The method of claim 2 further comprising, prior to positioning the sample:
   separating the sample from the substrate by ion beam milling;
   attaching a microprobe to the freed sample;
   extracting the sample from the substrate using the attached microprobe; and
   in which attaching the sample to a sample holder comprises attaching the sample to a sample holder and separating the microprobe from the attached sample.

8. The method of claim 7 in which rotating the sample about an axis perpendicular to the sample vertical axis to invert the top and bottom sides of the sample comprises inverting the sample by rotating the microprobe so that the orientation of the top and bottom sides is reversed.

9. The method of claim 1 in which milling the bottom side of the sample to remove at least of portion of the bottom surface of the sample to produce a uniformly flat surface comprises milling the bottom side of the sample using an ion beam having a first accelerating voltage and then milling the bottom side of the sample at a second accelerating voltage, the second accelerating voltage being less than half of the first accelerating voltage.

10. The method of claim 1 in which milling the bottom side of the sample to remove at least of portion of the bottom surface of the sample to produce a uniformly flat surface comprises milling the bottom side of the sample using an ion beam having an accelerating voltage of 5 kV or less.

11. The method of claim 1 in which milling the bottom side of the sample to remove at least of portion of the bottom surface of the sample to produce a uniformly flat surface comprises milling the bottom side of the sample using an ion beam having an accelerating voltage of 30 kV or more.

12. An apparatus for carrying out the method of claim 2.

13. A non-transitory computer-readable storage medium configured with a computer program, where the storage medium so configured causes a computer to control a charged particle beam system to carry out the steps of the method of claim 2.

14. A method of preparing an ultra thin TEM sample for TEM analysis, the method comprising:
   loading a substrate into an ion beam system including an ion beam source and optics for focusing an ion beam along an axis and onto the substrate;
   freeing a sample from the substrate by ion beam milling, said sample having a vertical axis, a top side closest to the ion beam source, and a bottom side opposite the ion beam source;
   attaching a microprobe to the freed sample;
   extracting the sample from the substrate using the attached microprobe;
   inverting the sample by rotating the microprobe so that the orientation of the top and bottom sides is reversed;
   attaching the inverted sample to a sample holder and separating the microprobe from the attached sample;
   positioning the sample holder so that the ion beam axis is at an angle of 30 to 90 degrees relative to the vertical axis of the sample;
   removing at least 25 nm from the bottom of the sample to produce a planar surface parallel to the ion beam axis;
   positioning the sample holder so that the top side of the sample is oriented opposite the ion beam source and so that the ion beam axis is parallel to the vertical axis of the sample;
   thinning the sample by directing the ion beam in a milling pattern that thins at least a portion of the sample to a thickness of 30 nm or less.

15. An apparatus for preparing ultra-thin TEM sample comprising:
   an ion beam system including an ion beam source, optics for focusing an ion beam along an axis and onto a substrate, and a micromanipulator for manipulating a sample; and
   a computer-readable memory storing computer instructions, the instructions including a program for controlling the apparatus and causing the apparatus to:
   position a sample having a vertical axis, a top side, and a bottom side so that the ion beam is transverse to the vertical axis of the sample;
   mill the bottom side of the sample to remove at least of portion of the bottom surface of the sample to produce a uniformly flat surface;
   position the sample so that the bottom side of the sample is oriented toward the ion beam source and so that the ion beam is parallel to the vertical axis of the sample; and
   thin the sample by directing the ion beam in a milling pattern that thins at least a portion of the sample to a thickness of 30 nm or less.

* * * * *